United States Patent [19]
Reiter et al.

[11] Patent Number: 6,100,061
[45] Date of Patent: Aug. 8, 2000

[54] RECOMBINANT CELL CLONE HAVING INCREASED STABILITY IN SERUM- AND PROTEIN-FREE MEDIUM AND A METHOD OF RECOVERING THE STABLE CELL CLONE AND THE PRODUCTION OF RECOMBINANT PROTEINS BY USING A STABLE CELL CLONE

[75] Inventors: Manfred Reiter; Wolfgang Mundt; Friedrich Dorner, all of Vienna, Austria

[73] Assignee: Immuno Aktiengesellschaft, Vienna, Austria

[21] Appl. No.: 09/100,253

[22] Filed: Jun. 19, 1998

[30] Foreign Application Priority Data

Jun. 20, 1997 [AT] Austria ..................................... 1073/97

[51] Int. Cl.⁷ ............................... C12P 21/02; C12N 5/10
[52] U.S. Cl. ....................... 435/69.1; 435/69.6; 435/455; 435/325; 435/352; 435/358; 435/383; 435/395; 435/404
[58] Field of Search ................................. 435/69.1, 69.6, 435/455, 325, 352, 358, 431, 383, 395, 404

[56] References Cited

U.S. PATENT DOCUMENTS

| | | | |
|---|---|---|---|
| 4,978,616 | 12/1990 | Dean, Jr. et al. | 435/70.3 |
| 5,393,668 | 2/1995 | Cinatl et al. | 435/402 |

FOREIGN PATENT DOCUMENTS

| | | |
|---|---|---|
| 96/15231 | 5/1996 | WIPO . |
| 96/26266 | 8/1996 | WIPO . |
| 97/05240 | 2/1997 | WIPO . |

OTHER PUBLICATIONS

K. Nakajima et al., "Medium for Producing Proteins by Recombinant Technology", Japanese Appln. 2696001 pp. 1–15, (Nov. 6, 1992).

B. Fischer et al., "FEBS Letters", Structural analysis of recombinant von Willebrand factor: identification of hetero– and homo–dimers, pp. 351:345–348, (1994).

Y. Ito et al., "Proc. Natl. Acad. Sci, USA", Protein–free cell culture on an artificial substrate with covalently immobilized insulin, pp. 93:3598–3601, (Apr. 1996).

H. Miyaji et al., "Cytotechnology", Expression of human beta–interferon in Namalwa KJM–1 which was adapted to serum–free medium, pp. 3:133–140, (1990).

H. Miyaji et al., Cytotechnology, Efficient expression of human beta–interferon in Namalwa KJM–1 cells adapted to serum–free medium by a dhfr gene coamplification method, pp. 4:173–180, (1990).

D.W. Murhammer et al., "Biotechnol. Prog.", Structural Features of Nonionic Polyglycol Polymer Molecules Responsible for the Protective Effect in Sparged Animal Cell Bioreactors, pp. 6:142–148, (1990).

T. Paterson, "Applied Microbiology and Biotechnology", Approaches to maximizing stable expression of a1–antitrypsin in transformed CHO cells, pp. 40:691–698, (1994).

M. Reiter et al., "Cytotechnology", Flow cytometry and two–dimensional electrophoresis (2–DE) for system evaluation of long term continuous perfused animal cell cultures in macroporous beads, pp.9:247–253, (1992).

T. Yamauchi et al., "Biosci. Biotech. Biochem.", Production of Human Antithrombin–III in a Serum–free Culture of CHO Cells, pp. 56(4):600–604, (1992).

Katinger et al. Advances in Molecular and Cell Biology 15A: 193–207 (1996).

Sinacore et al. Biotechnology and Bioengineering 52: 518–528 (1996).

*Primary Examiner*—David Guzo
*Attorney, Agent, or Firm*—Foley, Hoag & Eliot, LLP; Beth E. Arnold

[57] ABSTRACT

Disclosed are a stable recombinant cell clone which is stable in serum- and protein-free medium for at least 40 generations, a biomass obtained by multiplying the stable cell clone under serum- and protein-free culturing conditions, and a method of preparing recombinant proteins by means of the biomass. Furthermore, the invention relates to a method of recovering stable recombinant cell clones.

44 Claims, 3 Drawing Sheets

RECOMBINANT CELL CLONE HAVING INCREASED STABILITY IN SERUM- AND PROTEIN-FREE MEDIUM AND A METHOD OF RECOVERING THE STABLE CELL CLONE AND THE PRODUCTION OF RECOMBINANT PROTEINS BY USING A STABLE CELL CLONE

The present invention relates to a stable recombinant cell clone that is stable for at least 40 generations in serum- and protein-free medium, a biomass obtained by multiplying the stable cell clone under serum- and protein-free culturing conditions, and a method of preparing recombinant proteins by means of the biomass. Furthermore, the invention relates to a method of recovering stable recombinant cell clones. Furthermore, the invention relates to the production of a recombinant protein in a serum- and protein-free synthetic minimum medium.

The preparation of recombinant proteins, in particular of biomedical products, such as blood factors, is gaining in importance. To allow for an optimum growth of recombinant cells, serum is added to the medium in most instances. Because of the high costs of serum and for avoiding possible contaminations in the culturing medium by viral or molecular pathogens from the serum, a number of serum-free media have been developed which, in particular, should not contain any additives of bovine or human origin. In addition to the low risk of contaminating the prepared products with viral and molecular pathogens, the use of such media in the preparation process also allows for a simpler purification of the expressed proteins.

In most instances, recombinant cells are first cultured in serum-containing medium up to a high cell density, e.g. for a working cell bank, and subsequently they are re-adapted to serum-free medium during the production phase.

Miyaji et al. (1990. Cytotechnology 3:133–140) selected serum-independent cell clones in serum-free medium which contained insulin and transferrin. However, the living cell number and the expression rate proved to decrease continuously after 16 days. By co-amplification with a labelling gene, Mayaji et al. (1990. Cytotechnology 4:173–180) tried to improve the expression rate and the productivity of the recombinant cells.

Yamauchi et al. (1992. Biosci. Biotechnol. Biochem. 56:600–604) established serum-independent recombinant CHO sub-clones by culturing serum-dependent cells on microtiter plates as monolayer for 3 to 4 weeks in serum-free medium that contained human serum albumin, insulin and transferrin. Approximately 0.1% of the cells were serum-independent. Part of the subclones also grew in suspension culture in serum-free medium, yet the cells aggregated and formed lumps. The duplicating time of the cells amounted to 1.5 days. Yet there are no data either on the stability of the serum-independent clones obtained, nor on the long time cultivation of these clones under serum-free conditions.

Media which allow for the maintenance of the metabolic activity and for a growth of cells during the serum-free phase frequently contain additional substances, e.g. growth factors, such as insulin or transferrin, or adherence factors which substitute the serum components.

To avoid the addition of polypeptide factors, such as insulin or transferrin, and to allow for protein-free culturing conditions, various techniques have been developed. Thus, specifically defined, complete protein-free media have been developed which allow for a cell growth also under protein-free conditions.

WO 97/05240 describes the preparation of recombinant proteins under protein-free conditions, the cells co-expressing a growth factor in addition to the desired protein.

JP 2696001 describes the use of a protein-free medium for the production of factor VIII in CHO cells by adding a non-ionic surface-active agent or cyclodextrin to increase the productivity of the host cells. To increase the effectiveness of these additives, the addition of, e.g., butyrate and lithium is recommended.

WO 96/26266 describes the culturing of cells in a medium which contains a glutamin-containing protein hydrolysate whose content of free amino acids is less than 15% of the total weight of the protein, and whose peptides have a molecular weight of less than 44 kD. As the culturing medium for the cell cultures, a synthetic minimum medium is used as the basic medium to which, inter alia, fetal calf serum, gentamycine and mercapto-ethanol are added in addition to protein hydrolysate. The use of this serum-containing medium for the recombinant production of blood factors has not been mentioned.

U.S. Pat. No. 5,393,668 A describes special synthetic surfaces which allow for a growth of adherent cells under protein-free conditions.

To stimulate cell proliferation, CHO cells which over-express human insulin have been multiplied on an artificial substrate to which insulin is covalently bound (Ito et al. 1996 PNAS U.S.A. 93:3598–3601).

Reiter et al. (1992. Cytotechnology 9:247–253) describe the immobilisation of r-CHO cells first grown in serum-containing medium at a high density on carriers, and subsequent perfusion of the immobilized cells in protein-free medium during the production phase, wherein a continuous liberation of protein into the cell culture supernatant was found. There, the cells were perfused for less than 10 generations in protein-free medium.

Previous methods for the successful preparation of a large-scale cell culture under protein-free conditions have been described for continuous cell lines, in particular VERO cells (WO 96/15231). There, the cells are grown under serum- and protein-free conditions from the original ampoule up to a large technical scale of 1200 l. However, these are not recombinant cells, but host cells which are used for the production of virus antigen in a lytic process.

In contrast to adherent VERO cells, e.g. CHO cells are dependent on adhesion to a limited extent only. CHO cells grown by means of conventional methods under serum-containing conditions are capable of binding both to smooth and to porous micro-carriers (U.S. Pat. No. 4,978,616 A, Reiter et al. 1992. Cytotechnology 9:247–253). If CHO cells are grown under serum-free conditions, they lose this property and do not adhere to smooth carriers, such as, e.g., Cytodex 3, or they detach easily therefrom, unless adherence-promoting additives, such as, e.g., fibronectin, are put into the medium. Because of the slight adherence of CHO cells to carriers under serum-free conditions, the production of recombinant proteins thus mainly is effected in suspension culture. There, the production process may be effected as a continuous or as a batch-wise method. The recombinant cell culture at first is grown in a bioreactor up to an optimum cell density, optionally the protein expression is induced, and for harvesting, the medium containing the expressed proteins but also recombinant cells is withdrawn at certain intervals from the reaction tank and thus from the production process. By the continuous loss of biomass, the production efficiency in the bioreactor drops and increases again slowly only after the addition of fresh medium, since the cells must grow up to the desired cell density. Thus, despite the continuous process, repeatedly there is a phase of retardation, in which the production rate in this system drops. Furthermore, the growth and production capacity in such a system is limited by the maximum cell density attainable.

When adapting cells initially grown under serum-containing conditions to protein-free medium, it has repeatedly been found that the yield of expressed protein and the productivity of recombinant CHO cells greatly drops after adaptation in protein-free medium as compared to serum-containing conditions (Paterson et al. 1994. Appl. Microbiol. Biotechnol. 40:691–658). This is the consequence of an instability or reduced growth of the recombinant clones due to the changed culturing conditions. Despite the use of a stable original clone, on account of the altered fermentation conditions, repeatedly a large portion of the cells become cells with reduced expression or also non-producers, which overgrow product producers during the production process, whereby the fermenter culture finally largely consists of non-producers or of such cells having a low expression.

As a consequence, the maximum production capacity of the fermentation culture drops continuously, and a maximum product production is restricted to a certain number of generations or cell passages.

Thus, there is a need for a system in which a continuous production is possible over as long a period of time as possible, in particular in the large-scale production of recombinant proteins under serum- and protein-free conditions.

It would furthermore be desirable to obtain a recombinant cell clone which is stable in the production phase for many generations under protein-free conditions and which expresses recombinant protein.

Thus it is the object of the present invention to provide an efficient method of preparing recombinant proteins under serum- and protein-free cultivation and production conditions.

It is a further object to provide a stable recombinant cell clone.

According to the invention, this object is achieved by providing a recombinant cell clone obtainable from a cell culture that is obtained after culturing a recombinant original cell clone on serum-containing medium and re-adapting the cells to serum- and protein-free medium. The cells are continued to be cultured in serum- and protein-free medium under production equivalent conditions for at least 40 generations.

Preferably, culturing of the cells is effected without selection for the selection labelling and/or amplification gene, e.g. in the absence of MTX in case of CHO-dhfr⁻ cells.

By original cell clone within the scope of this invention a recombinant cell clone transfectant is understood which, upon transfection of host cells with a recombinant nucleotide sequence, expresses recombinant product in a stable manner under laboratory conditions. To optimize growth, the original clone is first grown in serum-containing medium. To increase the productivity, the original clone optionally is first grown in the presence of a selecting agent and selection for the selection marker and/or amplification marker. For the large-scale production, the original cell clone is first grown under serum-containing culturing conditions up to a high cell density, and shortly before the production phase it is re-adapted to serum- and/or protein-free medium. In this case, culturing is preferably effected without selection pressure.

It has been found that under these conditions, a large part of more than 95% of the cells become non-product producers in such a cell culture which has been re-adapted to serum- and protein free medium. By means of immune fluorescence with product-specific antibodies it could be shown that in dependence on the generation time of the cells in serum- and protein-free medium, the number of the non-producers rises in a culture and overgrows the product-producers, whereby the production capacity of the culture decreases.

The cell culture obtained after re-adaptation to serum- and protein-free medium is assayed for those cell clones of the cell population which are producers of the stable product under serum- and protein-free conditions, optionally in the absence of a selection pressure. This may be effected e.g. by means of immunofluorescence with labelled antibodies specifically directed against the recombinant polypeptide or protein. Those cells which have been identified as product producers are isolated from the cell culture and again multiplied under serum- and protein-free, optionally under production-equivalent, conditions. Isolation of the cells may be effected by isolating the cells and assaying for product-producers. Optionally, the cell culture containing the stable cells is again assayed for stable recombinant clones, and the latter are isolated from the cell culture and cloned. Subsequently, the stable recombinant cell clones obtained under serum- and protein-free conditions are further multiplied under serum- and protein-free conditions.

The recombinant cell clone according to the invention is characterized in that it is stable in serum-free and protein-free medium for at least 40, preferably at least 50, in particular more than 60 generations and expresses recombinant product.

According to a particular aspect of the invention, the stable recombinant cell clone is present in isolated form. Departing from the stable cell clone, a cell culture is obtained under serum- and protein-free conditions by multiplying the stable cells.

The stable recombinant cell clone of the invention preferably is derived from a recombinant mammalian cell. The recombinant mammalian cells may be all cells that contain sequences which encode a recombinant polypeptide or protein. Included are all continuously growing cells which grow adherently and non-adherently. Particularly preferred are recombinant CHO cells or BHK cells. Recombinant polypeptides or proteins may be blood factors, growth factors or other biomedically relevant products.

According to the present invention, stable recombinant cell clones are preferred which contain the encoding sequence for a recombinant blood factor, such as factor II, factor V, factor VII, factor VIII, factor IX, factor X, factor XI, protein S, protein C, an activated form of any one of these factors, or vWF, and which are capable of stable expression of this factor over several generations. Particularly preferred are recombinant CHO cells, which express vWF or a polypeptide having vWF activity, factor VIII or a polypeptide having factor VIII activity, vWF and factor VIII, factor IX or factor II.

The cell clone of the invention selected under serum- and protein-free conditions is particularly characterised in that it is stable in serum- and protein-free medium for at least 40, preferably for at least 50 generations, particularly preferred for more than 60 generations.

To provide a master cell bank, 30 generations are required. To carry out an average batch culture on a 1,000 liter scale, at least approximately 40 generations are required. Thus it has become possible for the first time to prepare with one individual clone a master cell bank (MCB), a working cell bank (WCB) including approximately 8 to 10 generations and thus, a production-scale cell culture (production biomass) with up to 20 to 25 generations under these conditions, since so far cell clones have become unstable after having grown on serum- or protein-free medium for some generations, or have exhibited a reduced viability, whereby a) no uniform cell culture with product producers, and b) no stable product productivity has been possible over an extended period of time.

The cell clone according to the invention thus is stable and productive for at least 40 generations under production conditions in serum- and protein-free medium. Previously described methods merely exhibited a product productivity for a generation number of less than 10 generations under protein-free conditions (Reiter et al. 1992, supra).

The criterion for stability is held to be a minimum number of at least 40 generations, preferably more than 50 generations, particularly preferred more than 60 generations in the production process, during which a stable expression of the proteins takes place and the cells do not exhibit any tumorogenic properties.

Surprisingly it has been found that the cell clone according to the invention exhibits an increased product productivity under serum- and protein-free conditions even in comparison to the original cell clone which had been cultured in serum-containing medium.

According to a further aspect, the present invention provides a cell culture containing at least 90%, preferably more than 95%, particularly preferred more than 98%, stable recombinant cells which are stable under serum- and protein-free conditions for at least 40 generations, in particular for at least 50 generations, and express recombinant product.

Within the scope of the present invention, by cell culture a master cell bank (MCB), a working cell bank (WCB) or a production biomass in a large-technical production bioreactor is understood.

According to the invention, the cell culture is particularly obtained by culturing a stable recombinant cell clone of the above-defined kind under serum- and protein-free conditions.

The cell culture of the invention is obtainable by multiplying the isolated stable cell clone from the individual clone, the seed cells up to the MCB, the WCB or a biomass on a production scale in the bioreactor under serum- and protein-free conditions, preferably without selection pressure on the selection and/or marker gene. In particular, it has been shown that the recombinant cells in a cell culture which are obtained departing from the stable recombinant clone of the invention are stable under serum- and protein-free conditions for at least 40 generations.

The cell culture provided according to the present invention, which has been prepared from a serum- and protein-independent stable cell clone, exhibits at least 90%, preferably at least 95%, particularly preferred at least 98%, stable recombinant cells under protein-free culturing and production conditions. By stable recombinant cells, in particular recombinant mammalian cells are understood which are derived from the stable cell clone. Preferred are recombinant CHO cells, preferably CHO-dhfr$^-$ cells, CHO-K1 cells and BHK cells that express a blood factor, preferably recombinant vWF, factor VIII, factor VIII and vWF, factor IX or factor II.

The cell culture according to the invention may contain the stable recombinant cells in the form of a suspension culture. The cells may also be immobilized on a carrier, in particular on a microcarrier, porous microcarriers being particularly preferred. Porous carriers, such as e.g. Cytoline® or Cytopore®, have proved to be particularly suitable.

According to a further aspect, the present invention provides a method for the large-technical production of a recombinant product under serum- and protein-free conditions, by using the stable cell clone according to the invention. The method comprises the steps of providing an isolated, stable recombinant cell clone of the above-defined kind for producing a cell culture. Multiplication of the isolated stable cell clone is effected from the stable individual cell clone up to the cell culture under serum- and protein-free conditions. In particular, also sub-culturing of the stable cell clones is effected under protein-free conditions, in particular without the addition of a protease, such as, e.g., trypsin. Thus it is ensured that at no time during the production of a cell culture used in the production of a recombinant product, a contamination occurs which possibly could be caused by the addition of serum- or protein-containing additives of human or animal origin to the cell culture. Thus, for the first time a method is described which allows for working under serum- and protein-free conditions, starting from the original clone, via the preparation of a working cell bank as far as to the production biomass and the subsequent production of recombinant protein.

The preparation of the recombinant products with the cell culture of the invention which contains more than 90%, preferably more than 95%, particularly preferred more than 98%, of stable product producer cells, may be effected as a suspension culture or with cells immobilized on carriers. The process may be effected as a batch-wise or a continuous method or by means of perfusion technique with serum- and protein-free medium.

The expressed recombinant proteins are then recovered from the cell culture supernatant, purified by means of methods known from the prior art, and further processed.

Any known synthetic medium can be used as the serum- and protein-free medium. Conventional synthetic minimum media may contain inorganic salts, amino acids, vitamins and a carbohydrate source and water. It may, e.g., be DMEM/HAM's F12 medium. The content of soybean or yeast extract may range between 0.1 and 100 g/l, particularly preferred between 1 and 5 g/l. As a particularly preferred embodiment, soybean extract, e.g. soybean peptone, may be used. The molecular weight of the soybean peptone is less than 50 kD, preferably less than 10 kD.

Particularly preferably a medium having the following composition is used: synthetic minimum medium (1 to 25 g/l) soybean peptone (0.5 to 50 g/l), L-glutamine (0.05 to 1 g/l), NaHCO$_3$ (0.1 to 10 g/l), ascorbic acid (0.0005 to 0.05 g/l), ethanol amine (0.0005 to 0.05), Na selenite (0.0001 to 0.01 g/l). Optionally, a non-ionic surface-active agent, such as, e.g., polypropylene glycol (PLURONIC F-61, PLURONIC F-68, SYNPERONIC F-68, PLURONIC F-71 OR PLURONIC F-108) may be added to the medium as a defoaming agent. This agent is generally applied to protect the cells from the negative effects of aeration, since without the addition of a surface-active agent, the rising and bursting air bubbles may damage those cells which are at the surface of these air bubbles. ("sparging"), (Murhammer and Goochee, 1990, Biotechnol. Prog. 6:142–148).

The amount of non-ionic surface-active agent may range between 0.05 and 10 g/l, particularly preferred is as low an amount as possible, between 0.1 and 5 g/l. Furthermore, the medium may also contain cyclodextrine or a derivative thereof. The addition of non-ionic surface-active agent or of cyclodextrine is, however, not essential to the invention. Preferably, the serum- and protein-free medium contains a protease inhibitor, such as, e.g., serine protease inhibitors, which are suitable for tissue culture and which are of synthetic or vegetable origin.

The parameters for culturing the cells, such as O$_2$ concentration, perfusion rate or medium exchange, pH, temperature and culturing technique will depend on the individual cell types used and may be determined by the skilled artisan in a simple manner. For instance, culturing of CHO cells may be effected in a stirring tank and under perfusion with protein-free medium at a perfusion rate of from 2 to 10 volume exchanges/day, at a pH of between 7.0 and 7.8, preferably at 7.4, and an $O_2$ concentration of between 40% up to 60%, preferably at 50%, and at a temperature of between 34° C. and 38° C., preferably of 37° C.

According to a further aspect, the present invention provides a method of recovering a stable recombinant cell clone, comprising the steps of multiplying a recombinant original clone up to the cell culture in serum-containing medium, preferably without selection pressure, culturing the cells under serum- and protein-free, preferably under production-equivalent, conditions, assaying the cell culture under serum- and protein-free conditions for product producers, cloning the stable recombinant cell clones under serum- and protein-free conditions, wherein cloning may be effected by generally known techniques, such as diluting out and growing the individual cell clones, multiplying the isolated cell clones under serum- and protein-free conditions, and optionally assaying the cell culture for product producers.

Only those recombinant cell clones are considered stable which express recombinant protein in a stable manner in protein-free medium for at least 10, preferably at least 20, and in particular at least 50 generations.

According to a further aspect, the invention relates to a method of recovering a stable recombinant cell clone, comprising the steps of multiplying a non-recombinant starting cell or cell line under serum- and protein-free conditions, and cloning a stable non-recombinant cell-clone under serum- and protein-free conditions, transfecting the stable cell clone with a recombinant nucleic acid and isolating stable recombinant cell clones, culturing the stable cell clone transfectants in serum- and protein-free medium, optionally under production-equivalent conditions, assaying the stable recombinant cells for production and product stability.

The invention will be described by way of the following examples, it is, however, not restricted to the examples.

a) F VIII-activity (mUnits/ml) and perfusion rate (1–5/day) over a period of 42 days.

b) Volumetric productivity (units factor VIII/l/day) in the perfusion bioreactor.

EXAMPLES

Example 1

Figure 1A:
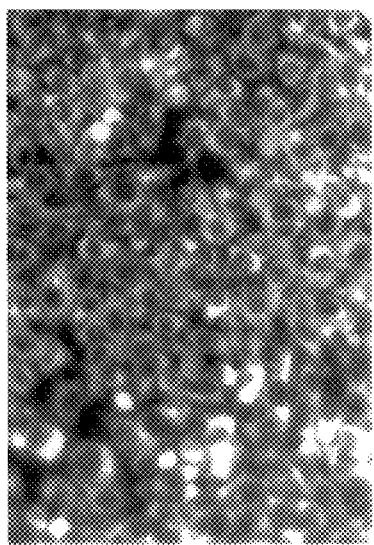
FIG. 1 (Parts A–C) shows the microscopy of a working cell bank of an original clone at the time of re-adaptation from serum-containing to serum- and protein-free medium (A), after 10 generations in serum and protein-free medium (B), and after 60 generations in serum- and protein-free medium (C).
Figure 1B:
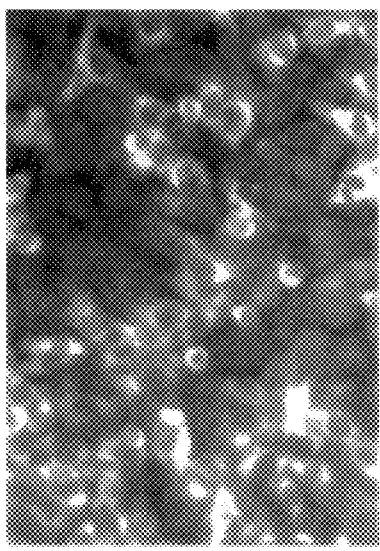
Figure 1C:

Stability of rvWF-CHO Cells After Re-Adaptation from Serum-Containing to Serum- and Protein-Free Medium CHO-dhfr⁻ cells were co-transfected with plasmids phAct-rvWF and pSV-dhfr, and vWF-expressing clones, as described in Fischer et al. (1994. FEBS Letters 351:345–348) were sub-cloned. From those sub-clones which expressed rvWF in a stable manner, a working cell bank (WCB) was set up under serum-containing conditions, yet in the absence of MTX., and the cells were immobilized on a porous microcarrier (Cytopore®) under serum-containing conditions. When a cell density of $2 \times 10^7$ cells/ml carrier matrix had been reached, readaptation of the cells to serum- and protein-free medium was effected. The cells were continued to be cultured for several generations under serum- and protein-free conditions. By means of immunofluorescence with labelled anti-vWF antibodies, the cells were assayed in serum- and protein-free medium at different points of time. The evaluation of the stability of the cells of the working cell bank was effected prior to medium readaptation, after 10 and after 60 generations in serum- and protein-free medium. Whereas the working cell bank still had 100% rvWF producers (FIG. 1A), the portion of rvWF producers after 10 generations in serum- and protein-free medium had decreased to approximately 50% (FIG. 1B). After 60 generations, more than 95% of the cells were identified as non-producers (FIG. 1C).

Example 2

Cloning of Stable Recombinant CHO Clones

Figure 2A:
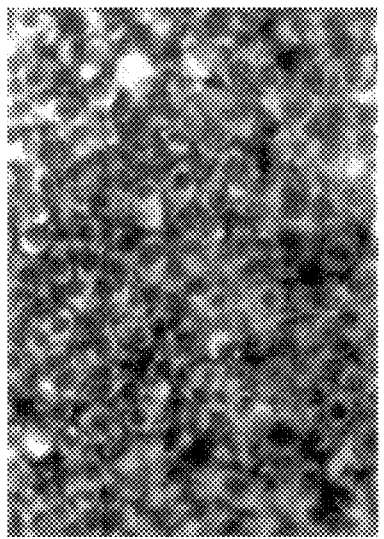
FIG. 2 (Parts A–C) shows the microscopy of a cell culture starting with a stable recombinant cell clone under serum- and protein-free conditions at the working cell bank stage (A), after 10 generations (B) and after 60 generations (C).
Figure 2B:
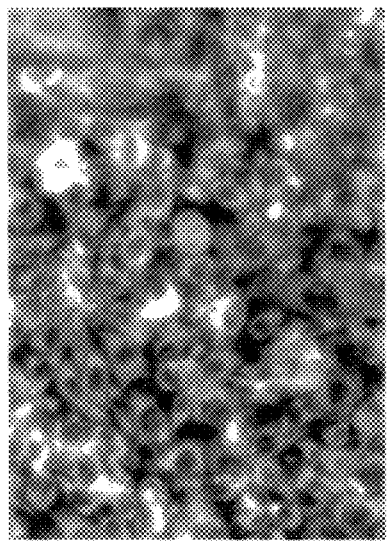
Figure 2C:
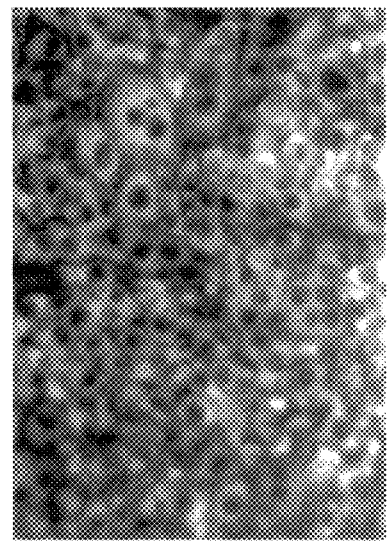

From the cell culture containing rvWF-CHO cells according to Example 1, which had been cultured for 60 generations in serum- and protein-free medium (FIG. 1C), a dilution was made, and 0.1 cells/well were each seeded in a micro-titer plate. The cells were cultured for approximately 3 weeks in DMEM/HAM's F12 without serum or protein additions and without selection pressure, and the cells were assayed by means of immunofluorescence with labelled anti-vWF antibody. A cell clone that had been identified as positive was used as the starting clone for the preparation of a seed cell bank. From the seed cell bank, a master cell bank (MCB) was prepared in serum- and protein-free medium, and individual ampoules were frozen off for the further preparation of a working cell bank. Departing from an individual ampoule, a working cell bank was prepared in serum- and protein-free medium. The cells were immobilized on porous microcarriers and continued to be cultured for several generations under serum- and protein-free conditions. At different points of time the cells were assayed for their productivity in serum- and protein-free medium by means of immunofluorescence with labelled anti-vWF antibodies. Evaluation of the stability of the cells was effected at the working cell bank stage and after 10 and 60 generations in serum- and protein-free medium. At the working cell bank stage (FIG. 2A) and also after 10 (FIG. 2B) and 60 generations (FIG. 2C), approximately 100% of the cells were identified as positive stable recombinant clones that express rvWF.

Example 3

Cell-Specific Productivity of the Recombinant Cell Clones

From defined stages during the culturing of recombinant cells, a defined number of cells was taken and incubated with fresh medium for 24 h. The rvWF:Risto-CoF activity was determined in the cell culture supernatants. Table 1 shows that the cell-specific productivity in the inventive stable recombinant cell clones was still stable even after 60 generations in serum- and protein-free medium and was even higher in comparison to the original clone that had been cultured in serum-containing medium.

The clone r-vWF-CHO F7 (see Table 1) was deposited in the European Collection of Cell Cultures (ECACC) on Jan. 22, 1998, and was assigned Deposit No. 98012206.

TABLE 1

| Cell clone | Cell specific productivity of the working cells mU rvWF/$10^6$ cells/day | Cell specific productivity after 10 generations mU rvWF/$10^6$ cells/day | Cell specific productivity after 60 generations mU rvWF/$10^6$ cells/day |
|---|---|---|---|
| rvWF-CHO #808.68 Original cell clone | 55 | 30 | <10 |
| r-vWF-CHO F7 Stable clone | 62 | 65 | 60 |

Example 4

Composition of a Synthetic Serum- and Protein-Free Medium:

| Component | g/l | Preferred amount (according to the knowledge at the time of application) in g/l |
|---|---|---|
| Synthetic minimum medium (DMEM/HAM's 12) | 1–100 | 11.00–12.00 |
| Soybean peptone | 0.5–50 | 2.5 |
| L-Glutamine | 0.05–1 | 0.36 |
| NaHCO$_3$ | 0.1–10 | 2.00 |
| Ascorbic acid | 0.0005–0.05 | 0.0035 |
| Ethanol amine | 0.0005–0.05 | 0.0015 |
| Na-selenite optional: | 0.0001–0.01 | 0.0086 |
| Synperonic F 68 | 0.01–10 | 0.25 |

Example 5

Culturing of rFVIII-CHO Cells in Protein- and Serum-Free Minimum Medium

A cell culture containing rFVIII-CHO cells was cultured in a 10 l stirring tank and with perfusion. A medium according to Example 4 was used. The cells were immobilized on a porous microcarrier (Cytopore®, Pharmacia) and cultured for at least 6 weeks. The perfusion rate was 4 volume exchanges/day, the pH was at 6.9–7.2, the O$_2$ concentration was approximately 20–50%, the temperature was 37° C.

Figure 3:
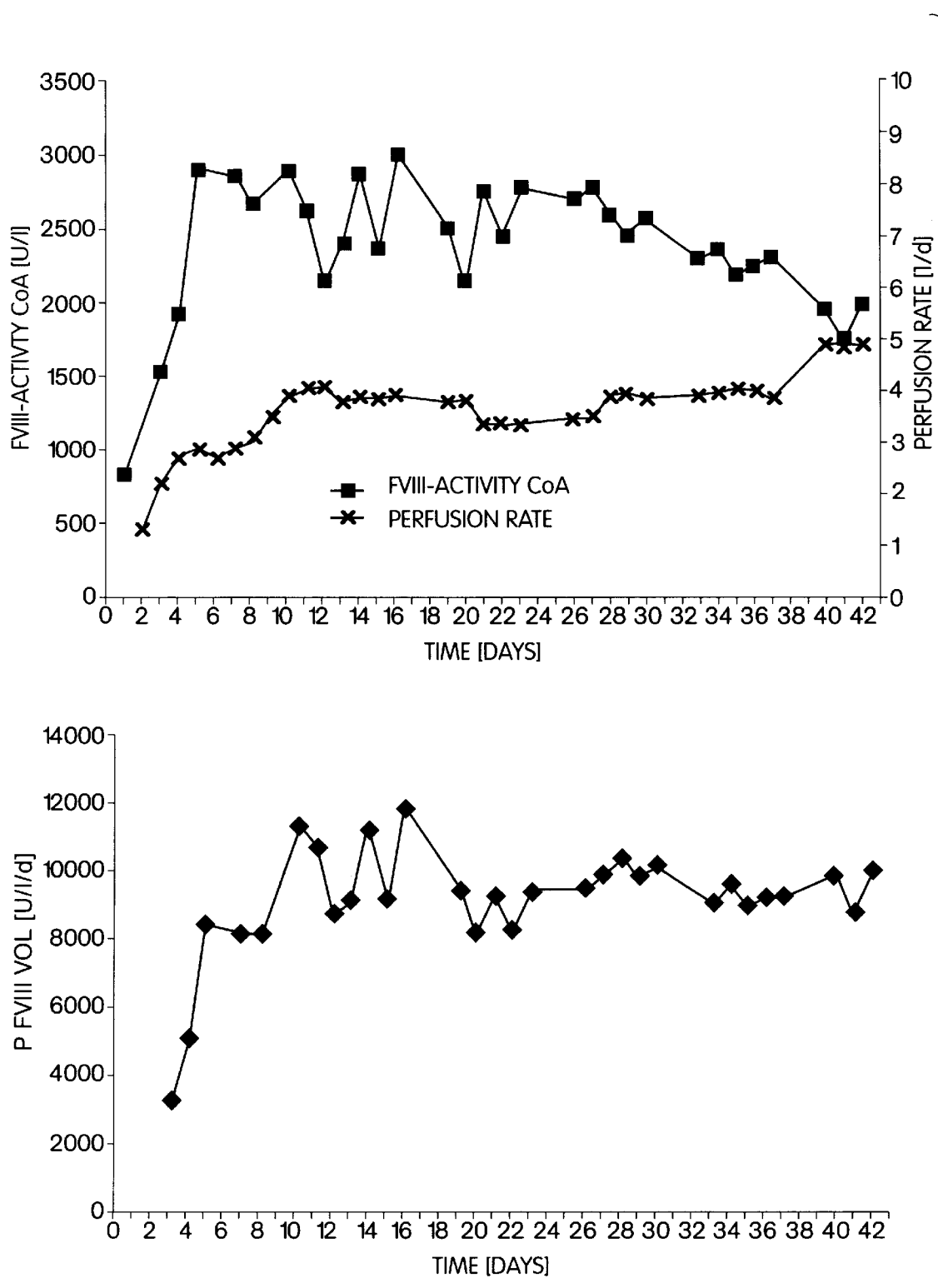
FIG. 3 (Parts a–b) shows the results of culturing an rFVIII-CHO cell clone in a 10 l perfusion bioreactor.

FIG. 3 shows the results of culturing an rFVIII-CHO clone in a 10 l perfusion bioreactor.

a) F VIII-activity (mUnits/ml) and perfusion rate (1–5/day) over a period of 42 days.

b) Volumetric productivity (units factor VIII/l/day) in the perfusion bioreactor.

| Days of culturing | Cell-specific productivity mU/$10^6$ cells/day) | Immunofluorescence (% FVIII-positive cells) |
|---|---|---|
| 15 | 702 | not indicated |
| 21 | 1125 | not indicated |
| 28 | 951 | >95% |

-continued

| Days of culturing | Cell-specific productivity mU/$10^6$ cells/day) | Immunofluorescence (% FVIII-positive cells) |
|---|---|---|
| 35 | 691 | >95% |
| 42 | 970 | not indicated |

Table 2 shows the stability and specific productivity of the rFVIII-expressing cells. For these results, samples were taken after 15, 21, 28, 35 and 42 days, centrifuged at 300 g and re-suspended in fresh serum- and protein-free medium. After further 24 h, the factor VIII concentration in the cell culture supernatants and the cell number were determined. Based on these data, the specific FVIII productivity was calculated.

A stable average productivity of 888 mUnits/$10^6$ cells/day was attained. This stable productivity was also confirmed by immunofluorescence with labelled anti-FVIII antibodies after 15, 21, 28, 35 and 42 days in serum- and protein-free medium.

What is claimed is:

1. A recombinant CHO cell clone stable in serum- and protein-free medium for at least 40 generations and expressing a recombinant product.

2. A recombinant CHO cell clone as set forth in claim 1, said cell clone being stable for at least 50 generations.

3. A recombinant CHO cell clone as set forth in claim 1, said cell clone being present in isolated form.

4. A recombinant CHO cell clone as set forth in claim 1, wherein said recombinant product is a recombinant polypeptide or a recombinant protein and said cell clone contains sequences encoding said recombinant polypetide or said recombinant protein.

5. A recombinant CHO cell clone as set forth in claim 1, wherein said recombinant CHO cell clone expresses von Willebrand factor as said recombinant product.

6. A recombinant CHO cell clone as set forth in claim 1, wherein said recombinant CHO cell clone expresses factor VIII as said recombinant product.

7. A recombinant CHO cell clone as set forth in claim 1, wherein said recombinant CHO cell clone co-expresses factor VIII and vWF as said recombinant product.

8. A recombinant CHO cell clone as set forth in claim 1, wherein said recombinant CHO cell clone expresses factor IX as said recombinant product.

9. A recombinant CHO cell clone as set forth in claim 1, wherein said recombinant CHO cell clone expresses factor II as said recombinant product.

10. A recombinant CHO cell clone as set forth in claim 1, obtainable by culturing a recombinant original cell clone on serum-containing medium so as to provide cells of a starting culture, and re-adapting said cells of said starting culture to serum- and protein free medium so as to provide a re-adapted cell culture, testing said re-adapted cell culture for stable product producer cells, and cloning a stable product producer cell clone under serum- and protein-free conditions from said stable product producer cells.

11. A recombinant CHO cell clone as set forth in claim 6, wherein said recombinant protein is a blood factor selected from the group consisting of factor II, factor V, factor VII, factor VIII, factor IX, factor X, factor XI, protein S, protein C, an activated form of any one of these factors, and vWF.

12. A recombinant CHO cell clone as set forth in claim 5, having ECACC Deposit No. 98012206.

13. A CHO cell culture comprising at least 90% of stable CHO recombinant cells, said stable recombinant cells being stable for more than 50 generations under serum- and protein-free conditions expressing recombinant product.

14. A cell culture as set forth in claim 13 obtainable by culturing a recombinant cell clone stable in serum- and protein-free medium for at least 40 generations, said stable recombinant cell clone expressing a recombinant product.

15. A cell culture as set forth in claim 13, obtainable by the steps of multiplying a recombinant original cell clone in serum-containing medium so as to obtain cells, culturing said cells under serum- and protein-free conditions so as to obtain a cell culture, assaying said cell culture under serum- and protein-free conditions for producers of said recombinant product, cloning stable cell clones under serum- and protein-free conditions, multiplying stable cell clones under serum- and protein-free conditions.

16. A cell culture as set forth in claim 13, wherein said recombinant CHO cells are CHO-DHFR⁻ cells or CHO-K1 cells.

17. A cell culture as set forth in claim 13, wherein said stable cells contain a sequence encoding a recombinant polypeptide or recombinant protein.

18. A cell culture as set forth in claim 13, wherein said cells are immobilized on a microcarrier.

19. A method of producing a recombinant product under serum- and protein-free conditions on a large technical scale comprising the steps of providing an isolated, stable recombinant original cell clone, said original cell clone being stable in serum- and protein-free medium for at least 40 generations and expressing a recombinant product, multiplying said original stable cell clone in serum- and protein-free medium so as to obtain a cell culture, culturing said cell culture containing stable cells in a bioreactor, thereby obtaining said recombinant product, and harvesting said recombinant product from a supernatant of said cell culture.

20. A method as set forth in claim 19, wherein said original cell clone is stable in serum- and protein-free medium for at least 50 generations.

21. A method as set forth in claim 19, wherein said serum- and protein-free medium is a synthetic mimimum medium.

22. A method as set forth in claim 19, wherein said serum- and protein-free medium contains a protease inhibitor.

23. A method of claim 19, wherein the stable cell clone is cultivated on a microcarrier.

24. A method as set forth in claim 21, wherein said synthetic minimum medium contains a yeast extract.

25. A method as set forth in claim 21, wherein said synthetic minimum medium contains a soybean extract.

26. A method of claim 21, wherein the serum- and protein-free medium further comprises peptone, L-Glutamine, NaHCO$_3$, Ascorbic acid, Ethanol amine, and Na-selenite.

27. A cell culture comprising more than 95% of stable recombinant cells, said stable recombinant cells being stable for more than 50 generations under serum- and protein-free conditions and expressing recombinant product.

28. A method for recovering a stable recombinant cell clone comprising the steps of multiplying a recombinant original cell clone in serum-containing medium so as to obtain a cell culture, culturing the cells of said cell culture under serum- and protein-free conditions, assaying said cell culture under serum- and protein-free conditions for producers of said recombinant product, cloning recombinant cell clones that are stable under serum and protein-free conditions, and multiplying said stable recombinant cell clones under serum- and protein-free conditions.

29. A method of claim 28, wherein the serum- and protein-free medium comprises minimum medium and peptone.

30. A method of claim 28, wherein the cells are cultivated on a microcarrier.

31. A method of recovering a stable recombinant cell clone comprising the steps of:

multiplying a non-recombinant original cell under serum- and protein-free conditions, cloning a stable, non-recombinant cell clone under serum- and protein-free conditions, transfecting said stable cell clone with a recombinant nucleic acid and isolating stable transfectants, culturing said isolated stable transfectants in serum- and protein-free medium, and assaying said cultured transfectants for production stability.

32. A method of claim 31, wherein the serum- and protein-free medium comprises minimum medium and peptone.

33. A serum- and protein-free synthetic medium comprised of minimum medium, soybean peptone, glutamine, sodium hydrogencarbonate, ascorbic acid, ethanol amine and sodium selenite.

34. A medium as set forth in claim 33, wherein said minimum medium comprises inorganic salts, amino acids, vitamins and a carbohydrate source.

35. A cell culture in a serum- and protein-free synthetic medium, said serum- and protein-free synthetic medium being comprised of minimum medium, soybean peptone, glutamine, sodium hydrogencarbonate, ascorbic acid, ethanol amine and sodium selenite.

36. A method of producing a recombinant polypeptide in a cell culture comprising the steps of multiplying a stable starting cell clone expressing a recombinant polypeptide serum- and protein-free medium so as to obtain a cell culture, culturing said cell culture containing stable cells in a bioreactor so as to obtain a cell culture, and harvesting said recombinant polypeptide from a supernatant of said cell culture.

37. A method as set forth in claim 36, wherein said recombinant polypeptide is a blood factor selected from the group consisting of factor II, factor V, factor VII, factor VIII, factor IX, factor X, factor XI, protein S, protein C and vWF or wherein said recombinant polypeptide is a polypeptide having the activity of said factors or an activated form of one of said factors.

38. A method as set forth in claim 36, wherein said stable starting cell clone is a recombinant CHO cell clone expressing von Willebrand factor as said recombinant polypeptide or expressing a polypeptide having von Willebrand factor activity.

39. A method as set forth in claim 36, wherein said stable starting cell clone is a recombinant CHO cell clone expressing factor VIII as said recombinant polypeptide or expressing a polypeptide having factor VIII activity.

40. A method as set forth in claim 36, wherein said stable starting cell clone is a recombinant CHO cell clone co-expressing factor VIII and vWF as said recombinant polypeptide.

41. A method as set forth in claim 36, wherein said stable starting cell clone is a recombinant CHO cell clone expressing factor IX as said recombinant polypeptide.

42. A method as set forth in claim 36, wherein said stable starting cell clone is a recombinant CHO cell clone expressing factor II as said recombinant polypeptide.

43. A method of claim 36, wherein the serum- and protein-free medium comprises minimum medium and peptone.

44. A recombinant CHO cell clone which has been cultivated in serum- and protein-free medium for at least 40 generations and which expresses a recombinant product.

* * * * *